United States Patent
Stark et al.

(10) Patent No.: US 12,237,071 B2
(45) Date of Patent: Feb. 25, 2025

(54) ELECTRO-OPTIC OBSERVATION DEVICE

(71) Applicant: Carl Zeiss AG, Oberkochen (DE)

(72) Inventors: Christoph Stark, Ellwangen (DE); Uwe Weber, Aalen (DE); Tammo Sebastian Lueken, Rosbach vor der Höhe (DE)

(*) Notice: Subject to any disclaimer, the term of this patent is extended or adjusted under 35 U.S.C. 154(b) by 215 days.

(21) Appl. No.: 18/102,651

(22) Filed: Jan. 27, 2023

(65) Prior Publication Data

US 2023/0238116 A1 Jul. 27, 2023

(30) Foreign Application Priority Data

Jan. 27, 2022 (DE) ...................... 10 2022 200 901.0

(51) Int. Cl.
| | | |
|---|---|---|
| *G06F 3/033* | (2013.01) | |
| *G02B 23/12* | (2006.01) | |
| *G06F 3/0362* | (2013.01) | |
| *G06F 3/0487* | (2013.01) | |
| *G16H 30/20* | (2018.01) | |

(52) U.S. Cl.
CPC ............. *G16H 30/20* (2018.01); *G02B 23/12* (2013.01); *G06F 3/0362* (2013.01); *G06F 3/0487* (2013.01); *G06T 2207/10* (2013.01)

(58) Field of Classification Search
CPC ... G06F 3/0362; G06F 3/0487; G02B 13/008; G02B 23/00; G02B 23/06; G02B 23/12; G06T 2207/10; G06V 10/147; F41G 1/32; F41G 1/38
See application file for complete search history.

(56) References Cited

U.S. PATENT DOCUMENTS

| | | | | |
|---|---|---|---|---|
| 4,965,439 A | * | 10/1990 | Moore | F41G 3/06 |
| | | | | 702/158 |
| 8,713,843 B2 | * | 5/2014 | Windauer | F41G 1/38 |
| | | | | 235/404 |
| 9,151,570 B2 | * | 10/2015 | Plaster | F41G 1/38 |
| 9,279,975 B2 | * | 3/2016 | Berlips | G02B 23/16 |
| 10,175,031 B2 | * | 1/2019 | VanBecelaere | F41G 1/38 |
| 10,942,006 B2 | * | 3/2021 | VanBecelaere | F41G 1/38 |

(Continued)

OTHER PUBLICATIONS

Office Action issued in German Patent Application No. DE 10 2022 200 901.0, dated Aug. 17, 2022 (from which this application claims priority) and English language translation thereof.

(Continued)

*Primary Examiner* — Joe H Cheng
(74) *Attorney, Agent, or Firm* — Ewers IP Law PLLC; Falk Ewers

(57) ABSTRACT

An electro-optic observation device, in particular a thermal imaging device, is provided. The electro-optic observation device includes a handheld device housing, a lens group arranged in the device housing on the entrance side, an image capture unit arranged in the device housing on the image side with respect to the lens group, an image display unit arranged in the device housing, an eyepiece arranged on the exit side with respect to the image display unit, and also a control device configured to control at least the image display unit depending on user-specifically variable parameters. In addition, the electro-optic observation device includes, as input means for varying the parameters, a rotary wheel accessible on the device housing for access by a user.

15 Claims, 2 Drawing Sheets

(56) References Cited

U.S. PATENT DOCUMENTS

| | | | |
|---|---|---|---|
| 11,966,038 B2* | 4/2024 | Hamilton | G02B 27/34 |
| 2005/0229468 A1* | 10/2005 | Zaderey | F41G 1/38 |
| | | | 42/122 |
| 2007/0235634 A1 | 10/2007 | Ottney et al. | |
| 2012/0097741 A1* | 4/2012 | Karcher | F41G 1/473 |
| | | | 235/404 |
| 2013/0033746 A1* | 2/2013 | Brumfield | G02B 23/105 |
| | | | 359/422 |
| 2013/0199074 A1* | 8/2013 | Paterson | F41G 1/38 |
| | | | 42/122 |
| 2015/0369565 A1 | 12/2015 | Kepler | |
| 2019/0394376 A1 | 12/2019 | Reed et al. | |
| 2024/0056678 A1* | 2/2024 | Burger | G01P 15/18 |

OTHER PUBLICATIONS

Decision to Grant issued in German Patent Application No. DE 10 2022 200 901.0, dated Feb. 16, 2023 (from which this application claims priority) and English Language Translation thereof.

* cited by examiner

ELECTRO-OPTIC OBSERVATION DEVICE

CROSS REFERENCE TO RELATED APPLICATIONS

This application claims priority to German patent application 10 2022 200 901.0, filed Jan. 27, 2022, the entire content of which is incorporated herein by reference.

TECHNICAL FIELD

The disclosure relates to an electro-optic observation device.

BACKGROUND

Optical observation devices are used during observation of nature and animals and (e.g., also in association therewith) also during hunting. Such observation devices are often binoculars or spotting scopes (the latter are commonly also referred to as "telescopes"). In the case of electro-optic observation devices, the functional scope thereof is often extended in order that "phenomena" outside the visual spectral range or below a brightness required for the human eye are made accessible to a user. In particular, mention may be made here of the representation of heat signatures and/or residual-light-intensified images which make it possible to observe objects even in (in particular subjective) darkness. Such functions are usually used in thermal imaging devices or else in night vision devices. In this case, usually in a departure from purely optical observation devices the incident radiation is passed on to a person using the observation device (for short: a user) not by optical means but rather indirectly via image converter devices. In such cases, therefore, the image that can be viewed by the user is usually a display generated on the basis of the incident radiation and usually after processing (image processing) has been carried out.

In the case of modern electro-optic observation devices, the user usually has the possibility of adapting the—often electronically generated—display at least in part to said user's requirements, e.g., a brightness, a contrast, a magnification factor or the like. In this case, in a manner similar to that in the case of a camera, the user can often select and vary settings (usually formed by variable parameters) on the basis of a menu represented within the display. For this purpose, pushbuttons used for menu navigation, in particular for selecting and adapting the settings, are usually arranged on the observation device.

SUMMARY

It is an object of the disclosure to improve convenience of use of an electro-optic observation device.

This object is achieved by an electro-optic observation device as described herein.

The electro-optic observation device according to an aspect of the disclosure typically constitutes a thermal imaging device. Optionally, the electro-optic observation device constitutes a night vision device (used to display residual-light-intensified recordings in particular in the visual spectral range) or else a combination of these devices. The electro-optic observation device further optionally constitutes a further combined device, a so-called "fusion system", in which a (in particular digital) recording of the visual spectral range is combined ("fused", e.g., superimposed) with a (in particular digitally) recorded thermal image and displayed.

The electro-optic observation device according to an aspect of the disclosure includes a handheld device housing (i.e., a device housing which can be gripped or held by a hand or is at least handleable by a person), at least one lens group arranged in the device housing on the entrance side, and at least one image capture unit arranged in the device housing on the image side with respect to the lens group. Furthermore, the observation device includes an image display unit arranged in the device housing, an eyepiece arranged on the exit side with respect to the image display unit, and a control device configured to control at least the image display unit depending on user-specifically variable parameters. In addition, the observation device includes, as input means for varying the parameters, a rotary wheel accessible on the device housing for access by a user.

The use of a rotary wheel is advantageous to the effect that the rotation of a wheel for maneuvering through a menu constitutes intuitive operation. In this case, it is usually not necessary to look at the setting element, i.e., the rotary wheel. The use and operation of the observation device thus become particularly convenient. Furthermore, at least two functions, in particular maneuvering through a menu in opposite directions, can be integrated into one operating element (the rotary wheel) and structural space—at least on a housing outer surface (casing surface)—can also be saved as a result.

The observation device forms in particular a spotting scope, i.e., a monocular "telescope", e.g., a thermal imaging spotting scope. Alternatively, however, the observation device can also be configured for binocular observation.

In an exemplary embodiment of the disclosure, the control device is configured to predefine (in particular represent) a menu structure which is represented in a ring-band-like manner and which, in reaction to a rotation of the rotary wheel, switches between menu items arranged along the ring-band-like representation. In particular, therefore, with the image display unit—e.g., partly or completely superimposed over the image that is captured with the image capture unit and is to be displayed—a kind of strip or else a ring band is displayed, on which individual menu items are successively arranged. If the rotary wheel is moved, said menu items are highlighted successively according to their order and/or are moved to a highlighted position within the display (e.g., into the center of the display). This gives the impression that the strip is moving, or the ring band is rotating. This enables particularly intuitive operation with the use of the rotary wheel.

In one exemplary embodiment of the disclosure, the rotary wheel is configured to be rotatable without stops. To put it another way, the rotary wheel can be rotated continuously in both directions of rotation. As a result, different numbers of selectable menu items and/or setting options can be mapped to the rotation of the rotary wheel in a particularly simple manner.

Typically, a digital encoder is used for capturing and/or evaluating the rotation of the rotary wheel. Typically, the encoder is an incremental encoder. Alternatively, the encoder is configured in analogue fashion and/or as an absolute value encoder.

Typically, the rotary wheel also has haptic feedback in order to indicate individual rotary positions to the user.

In one exemplary embodiment of the disclosure, the menu structure (in particular the representation thereof)—in particular with the control unit—is predefined with end stops.

That is to say that the strip or else the ring band do not "move" beyond the corresponding first or last menu item.

In an alternative exemplary embodiment of the disclosure, the menu structure is predefined so as to be closed in a ring-like manner and continuously rotatable (or else traversable). That is to say that in the event of going beyond the first or last menu item with the rotary wheel, the menu "jumps" ahead (or back) to the opposite menu item (i.e., the last or respectively the first), thereby giving the impression that the menu structure can rotate continuously in a circle. This is particularly user-friendly in particular in the case of a comparatively high number (e.g., more than 5 or 10 menu items), since the menu structure cannot be searched exclusively backwards or forwards from the "ends of a list of menu items". Applied figuratively to the selection of letters of the alphabet, it may be easier for a user to be able to jump from position A to X by a "short route" via Z and Y compared with via B, C, D, etc.

In one exemplary embodiment of the disclosure, the control device is configured, in the event of a menu item being chosen, to vary a parameter assigned to said menu item depending on a (in particular further) rotation of the rotary wheel. In particular, in this case, the control device is configured to display a current setting of the parameter in the manner of a circle chart. An end stop in terms of software is optionally provided in this case, such that the values of the respective parameter can be increased or decreased only between the two extrema (as "end values") with the rotary wheel. Alternatively, however, the selection of the respective parameter values is also configured here to be continuous, also "freely rotating" in relation to the circle charts mentioned above, such that in the event of the maximum value being exceeded, there is a jump back to the minimum value (and vice versa).

In a further exemplary embodiment, the rotary wheel partly projects beyond an exterior casing surface of the device housing. In particular, in this case, the axis of rotation of the rotary wheel is typically embedded, i.e., arranged below the casing surface. Typically, less than two thirds of the diameter of the rotary wheel projects beyond the casing surface. In this context, casing surface is understood to mean, in particular, a kind of envelope surface. In this regard, the rotary wheel can be arranged in a kind of incision or depression in the device housing and can project only with a comparatively small projection, e.g., less than one quarter of the diameter, beyond the envelope surface (in particular spanning the depression), but can nevertheless be accessible to the extent of, for example, approximately one third or half of the circumference (namely in said depression).

In addition, for the case where the rotary wheel is arranged on the image side (or "ahead") of the image capture unit, the rotary wheel is expediently arranged in such a way that it does not intervene in the beam path of the lens group.

Furthermore, the rotary wheel has in particular a diameter value of between 5 and 50 millimeters, typically between 10 and 30 millimeters.

In one exemplary embodiment of the disclosure, the rotary wheel is mounted fluid-tightly in order to prevent liquids and/or contaminants from penetrating into the device housing.

In a further exemplary embodiment of the disclosure, the rotary wheel is operable only (i.e., exclusively) rotationally.

Typically, the observation device includes, as additional input means for varying the parameters (and in particular for maneuvering through the menu structure), a button accessible on the device housing for access by a user. Said button embodies a switch, in particular, and in this case is typically designed in the form of a pushbutton, rocker switch, a membrane switch or the like. In particular, said button serves to "confirm", i.e., select, menu items and/or parameter values chosen with the rotary wheel. This is expedient in particular for the case where the rotary wheel is operable only rotationally.

In an exemplary embodiment of the disclosure, the rotary wheel is operable as a pushbutton in addition to the rotational operation. In this case, the rotary wheel can be "pressed" (i.e., actuated) transversely and/or parallel to its axis of rotation. In this case, the button described above can be omitted. A selection or confirmation of a chosen menu item or parameter value is performed in this case by pressure actuation of the rotary wheel.

In one exemplary embodiment of the disclosure, the axis of rotation of the rotary wheel is oriented parallel to an at least theoretical radiation transmission direction of the device housing. "Theoretical" is used here against the background that there is no complete transmission of radiation through the device housing.

Alternatively, the axis of rotation of the rotary wheel is oriented in a manner following the local inclination of the casing surface in relation to the radiation transmission direction. As a further alternative, the orientation of the axis of rotation is also chosen depending on the positioning on the device housing in relation to the user's finger that is to be used as intended. In this regard, for example, the rotary wheel which is intended to be operated by a thumb is inclined to a comparatively great degree, e.g., between 45 and 90 degrees, in relation to the radiation transmission direction, while the rotary wheel which is intended to be operated by the index finger is oriented, rather, parallel to the radiation transmission direction.

In one exemplary embodiment of the disclosure, the observation device, as already mentioned above, is configured for observation in the infrared spectral range, i.e., forms the thermal imaging device described above. For this purpose, expediently, the lens group and/or the image capture unit are/is configured for capturing radiation from the infrared spectral range. By way of example, correspondingly suitable coatings on optically active surfaces of the lens group are used for this purpose. In this case, the image capture unit is typically an image sensor which is configured for capturing IR radiation, e.g., is embodied without IR filters.

Particularly in the case of the night vision device, the image capture unit is expediently formed by an image intensifier (also referred to as residual light intensifier) for the visual spectral range. In particular, in this case, the image capture unit is a combination of such an image intensifier with an (in particular digital) image sensor. Alternatively, however, in a known manner, the image intensifier in this case forms both the image capture unit and the image display unit.

In a further exemplary embodiment, in which the observation device forms the fusion system, the control device is configured, as mentioned above, to combine, in particular superimpose, the recording of the visual spectral range with the (in particular digital) recording of the infrared spectral range (the actual thermal image), and to display the result on the image display unit.

In the case of the fusion system, the observation device expediently includes a first lens group for the visual spectral range and typically also an assigned image capture unit, and a second lens group, in particular for the infrared spectral range, and typically also a second, correspondingly assigned image capture unit. Typically, both lens groups each form an objective lens for the respective spectral range. In particular, therefore, two "optical spectral channels" are formed, the image representations of which are typically also captured separately with the correspondingly assigned image capture unit. In particular, the second lens group and optionally the second image capture unit are embodied as described above with respect to the thermal imaging device.

Here and hereinafter, the conjunction "and/or" should be understood to mean in particular that the features linked by this conjunction can be embodied both jointly and as alternatives relative to one another.

BRIEF DESCRIPTION OF THE DRAWINGS

The disclosure will now be described with reference to the drawings wherein.

DESCRIPTION OF EXEMPLARY EMBODIMENTS

Mutually corresponding parts are provided with the same reference signs throughout the figures.

Figure 1:
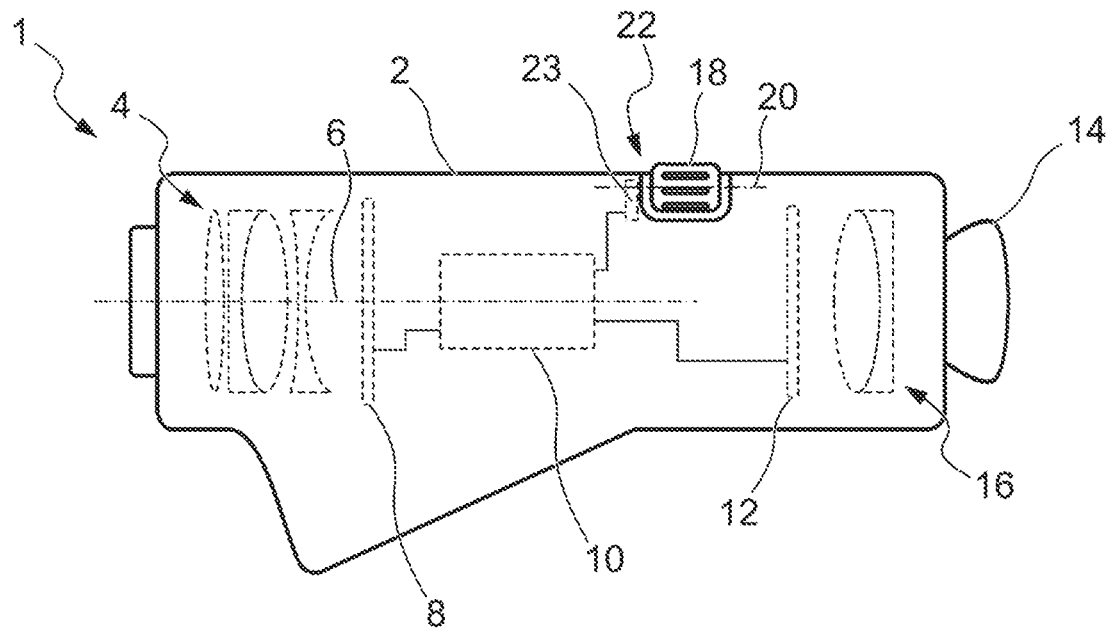
FIG. 1 shows a schematic side view of an electro-optic observation device.

FIG. 1 schematically illustrates an electro-optic observation device, here specifically a thermal imaging spotting scope (for short: thermal imaging device 1). The thermal imaging device 1 includes a handheld device housing (for short: housing 2). An entrance-side lens group 4 and, downstream in a "radiation transmission direction 6", an image capture unit in the form of an image sensor 8 are arranged in the housing 2. The image sensor 8 is coupled to a control device (referred to here as "controller 10") in terms of signal transmission. The controller 10 is coupled on the output side to an image display unit, here in the form of a display 12, and is configured to process an image received with the image sensor 8 and to output said image in processed form to the display 12 for the purpose of being displayed. Furthermore, the thermal imaging device 1 includes an eyepiece 14 (and, in the exemplary embodiment illustrated, a "second" lens group 16 assigned to the eyepiece 14), through which a user can view the processed and displayed image.

In order to be able to effect settings on the displayed image, i.e., in order to be able to user-specifically adapt the display of said image, the thermal imaging device 1 furthermore includes a rotary wheel 18 as setting means. The latter is arranged on the exterior of the housing 2 in a manner accessible to a user. In the present exemplary embodiment, an axis of rotation 20 of the rotary wheel 18 is oriented parallel to the radiation transmission direction 6. In this case, the rotary wheel 18 is arranged in a depression 22 in the housing 2, such that only a comparatively small portion, for example approximately one sixth of the diameter of the rotary wheel 18, projects beyond an outer surface or casing surface of the housing 2. In the depression 22 (recessed relative to the casing surface) a relatively large region of the rotary wheel 18 is nevertheless accessible to the user.

In the exemplary embodiment illustrated, the rotary wheel 18 has a plurality of discrete rotary positions which are delimited from one another in a manner recognizable to the user by way of haptic feedback. In addition, the rotary wheel 18 is actuable as a pushbutton perpendicularly to the axis of rotation 20. Furthermore, the rotary wheel 18 is coupled to a digital incremental encoder 23, which is in turn coupled to the controller 10 for the evaluation of the rotation of the rotary wheel 18.

Figure 2:
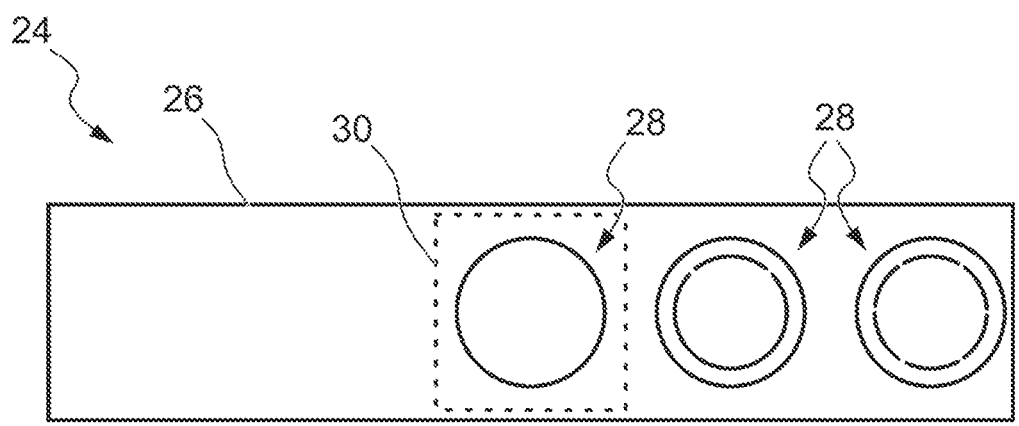
FIGS. 2 and 3 each show a schematic illustration of a display of a menu structure in two different selection stages, said display being generated in the observation device.
Figure 3:
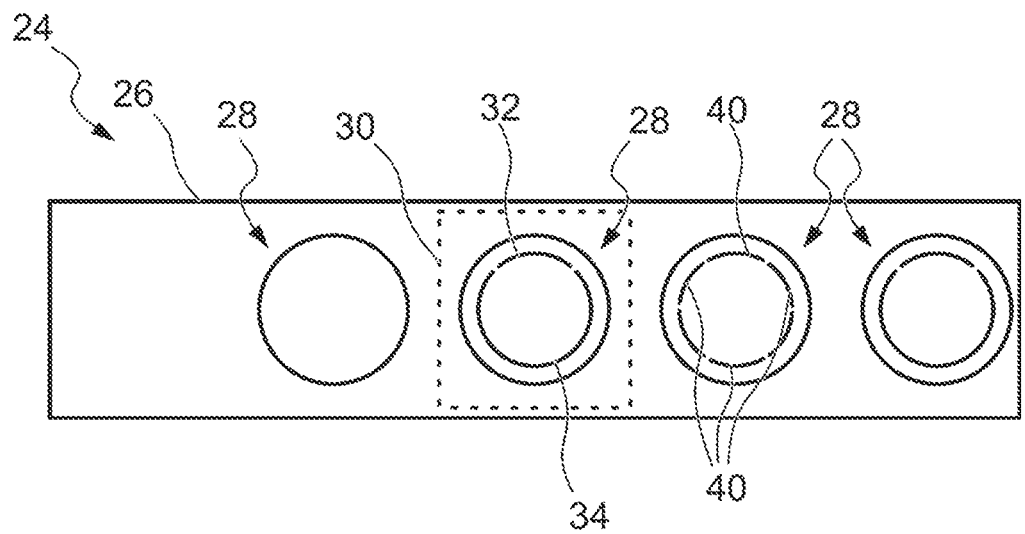

The rotary wheel 18 serves for maneuvering through a menu structure 24 defined on the part of the controller 10, the representation of said menu structure, which representation is visualized with the display 12, being illustrated schematically in FIGS. 2 and 3. In this case, the menu structure 24 is firstly formed by a band 26 which is inserted instead of the image to be displayed or is superimposed over said image. The menu structure 24 is displayed on the display 12 by the controller 10 if the rotary wheel 18 is actuated.

Individual menu items 28 are arranged successively on the band 26. The menu items 28 afford the possibility, inter alia, of varying parameters (e.g., brightness, color, contrast, sharpness, etc.) for displaying the image with the display 12. Upon rotation of the rotary wheel 18, the menu items 28, according to their order and the implemented angle of rotation of the rotary wheel 18, switch to a highlighted region, e.g., one that is illuminated or identified in some other way (indicated by a box 30 depicted by dashed lines). Between FIGS. 2 and 3, the rotary wheel 18 was thus moved to an extent such that a directly succeeding menu item 28 was put into the highlighted region, i.e., into the box 30.

Figure 4:
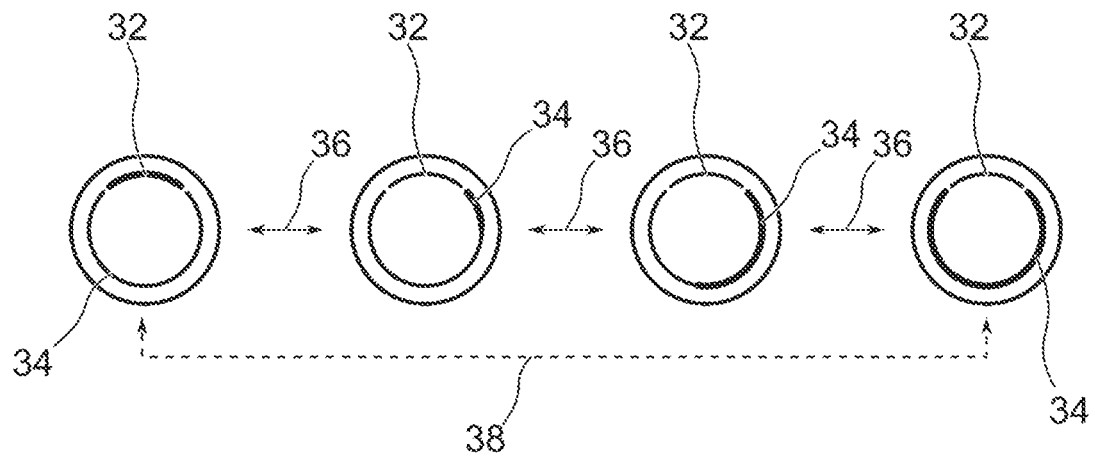
FIG. 4 shows a schematic illustration of setting possibilities for a selected menu item of the menu structure.

The menu item 28 chosen, i.e., moved into the box 30, is selected by the rotary wheel 18 being pressed. The selected menu item 28 illustrated in FIG. 3 represents the display parameter "brightness". In this case, the desired value is in turn set with a rotation of the rotary wheel 18. The display of the possible values, specifically the setting possibilities thereof, is modelled on a circle chart. In this regard, an automatic mode 32 is typically in an upper region (indicated by a greater line width of the chosen "value range" in FIG. 4). Further rotation of the rotary wheel 18 is accompanied by switching from the automatic mode 32 into an individual region 34. The latter is indicated by an approximately three-quarter circle line. The further the rotary wheel 18 is rotated (here in the clockwise direction) (indicated by the solid double-headed arrows 36), the further the individual region 34 "fills up" (i.e., the larger a proportion of the three-quarter circle line becomes, said proportion being represented with a greater line width; see FIG. 4) and the larger the set value becomes.

In this case, two different exemplary embodiments of the menu navigation are provided. One exemplary embodiment thereof is an embodiment with "stop". In the case of brightness, here a further rotation of the rotary wheel 18 given complete "filling" of the three-quarter circle line does not result in a further increase or change in the values. For a reduction of the values, the rotary wheel 18 would have to be turned back again (cf. double-headed arrows 36).

The alternative exemplary embodiment is a continuous rotation of the "values". After complete filling (i.e., the maximum value) has been attained, in the present example of brightness, the "selection" upon further rotation of the rotary wheel 18 jumps again to the automatic mode 32 or beyond the latter again to the low values of the brightness (correspondingly conversely upon rotation in the opposite direction beyond the minimum value). This continuous exemplary embodiment is indicated by the additional arrow 38 depicted by a dashed line.

The color of the display can be set in a further menu item 28. In this case, as an alternative to the above-described setting of the brightness, a plurality of individual "color fields 40" are able to be chosen, but further "fine setting" is no longer provided within these color fields 40.

The subject matter of the disclosure is not restricted to the exemplary embodiments described above. Rather, further embodiments of the disclosure can be derived from the above description by a person skilled in the art. In particular, the individual features of the disclosure described with reference to the various exemplary embodiments and the design variants thereof can also be combined with one another in a different way.

LIST OF REFERENCE NUMERALS

1 Thermal imaging device
2 Housing
4 Lens group
6 Radiation transmission direction
8 Image sensor
10 Controller
12 Display
14 Eyepiece
16 Lens group
18 Rotary wheel
20 Axis of rotation
22 Depression
23 Incremental encoder
24 Menu structure
26 Band
28 Menu item
30 Box
32 Automatic mode
34 Individual region
36 Double-headed arrow
38 Double-headed arrow
40 Color field

What is claimed is:

1. An electro-optic observation device, comprising:
a handheld device housing;
a lens group arranged in the handheld device housing on an entrance side;
an image capture unit arranged in the handheld device housing on an image side with respect to the lens group;
an image display unit arranged in the handheld device housing;
an eyepiece arranged on an exit side with respect to the image display unit;
a control device configured to control at least the image display unit depending on user-specifically variable parameters; and
as input means for varying the parameters, a rotary wheel accessible on the handheld device housing for access by a user.

2. The electro-optic observation device according to claim 1, wherein the control device is configured to predefine a menu structure which is represented in a ring-band-like manner and which, in reaction to a rotation of the rotary wheel, switches between menu items arranged along the ring-band-like representation.

3. The electro-optic observation device according to claim 2, wherein the menu structure is predefined with end stops.

4. The electro-optic observation device according to claim 2, wherein the menu structure is predefined so as to be closed in a ring-like manner and continuously rotatable.

5. The electro-optic observation device according to claim 2, wherein the control device is configured, in the event of a menu item being chosen, to vary a parameter assigned to said menu item depending on a rotation of the rotary wheel, and
wherein the control device is configured to display a current setting of the parameter in the manner of a circle chart.

6. The electro-optic observation device according to claim 1, wherein the rotary wheel is configured to be rotatable without stops.

7. The electro-optic observation device according to claim 1, wherein the rotary wheel partly projects beyond an exterior casing surface of the handheld device housing.

8. The electro-optic observation device according to claim 1, wherein the rotary wheel is mounted fluid-tightly.

9. The electro-optic observation device according to claim 1, wherein the rotary wheel is operable only rotationally.

10. The electro-optic observation device according to claim 9, further comprising:
as additional input means for varying the parameters, a button accessible on the handheld device housing for access by a user.

11. The electro-optic observation device according to claim 1, wherein the rotary wheel is operable as a pushbutton in addition to a rotational operation.

12. The electro-optic observation device according to claim 1, wherein an axis of rotation of the rotary wheel is oriented parallel to an at least theoretical radiation transmission direction of the handheld device housing.

13. The electro-optic observation device according to claim 1, wherein at least one of the lens group and the image capture unit is configured for capturing radiation from an infrared spectral range, and
wherein the observation device forms a thermal imaging device.

14. The electro-optic observation device according to claim 1, wherein the image capture unit is formed by an image intensifier for an visual spectral range.

15. The electro-optic observation device according to claim 1, wherein the control device is configured to combine a recording of an visual spectral range with a recording of an infrared spectral range and to display the result on the image display unit.

* * * * *